(12) United States Patent
Dionne et al.

(10) Patent No.: US 9,410,256 B2
(45) Date of Patent: *Aug. 9, 2016

(54) ULTRASOUND AND ACOUSTOPHORESIS FOR WATER PURIFICATION

(71) Applicant: FloDesign Sonics, Inc., Wilbraham, MA (US)

(72) Inventors: Jason Dionne, Simsbury, CT (US); Bart Lipkens, Hampden, MA (US); Edward Rietman, Nashua, NH (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/221,527

(22) Filed: Mar. 21, 2014

(65) Prior Publication Data

US 2014/0202876 A1 Jul. 24, 2014

Related U.S. Application Data

(62) Division of application No. 12/947,757, filed on Nov. 16, 2010, now Pat. No. 8,691,145.

(60) Provisional application No. 61/261,686, filed on Nov. 16, 2009, provisional application No. 61/261,676, filed on Nov. 16, 2009.

(51) Int. Cl.
*C25B 9/00* (2006.01)
*A61L 2/025* (2006.01)
(Continued)

(52) U.S. Cl.
CPC . *C25B 9/00* (2013.01); *A61L 2/025* (2013.01); *C01B 13/11* (2013.01); *C02F 1/36* (2013.01); *C12M 47/02* (2013.01); *C25B 1/13* (2013.01); *C02F 1/4672* (2013.01); *C02F 1/78* (2013.01); *C02F 2001/46138* (2013.01);
(Continued)

(58) Field of Classification Search
CPC ................. A61L 2/025; B01D 49/006; B01D 2259/816; B01D 43/10; B01J 19/10; C02F 1/36; C25B 9/00; C25B 1/13; C12M 47/02; C01B 13/11
See application file for complete search history.

(56) References Cited

U.S. PATENT DOCUMENTS 2,667,944 A 2/1954 Crites
3,555,311 A 1/1971 Weber
(Continued)

FOREIGN PATENT DOCUMENTS

DE 30 27 433 A1 2/1982
EP 0 292 470 B1 11/1988
(Continued)

OTHER PUBLICATIONS

B. Lipkens, J. Dionne, A. Trask, B. Szczur, A. Stevens, and E. Rietman, "Separation of micronsized particles in macro-scale cavities by ultrasonic standing waves," Presented at the International Congress on Ultrasonics, Santiago, Jan. 11-17, 2009.

(Continued)

*Primary Examiner* — Regina M Yoo
(74) *Attorney, Agent, or Firm* — Richard M. Klein; Fay Sharpe LLP

(57) ABSTRACT

Provided herein are systems and methods for separation of particulate from water using ultrasonically generated acoustic standing waves.

48 Claims, 11 Drawing Sheets

(51) Int. Cl.

| | | |
|---|---|---|
| *C01B 13/11* | (2006.01) | |
| *C02F 1/36* | (2006.01) | |
| *C25B 1/13* | (2006.01) | |
| *C12M 1/00* | (2006.01) | |
| *C02F 1/467* | (2006.01) | |
| *C02F 1/78* | (2006.01) | |
| *C02F 1/461* | (2006.01) | |

(52) U.S. Cl.
CPC .... *C02F 2201/782* (2013.01); *C02F 2209/006* (2013.01); *C02F 2209/008* (2013.01); *C02F 2303/04* (2013.01)

(56) References Cited

U.S. PATENT DOCUMENTS

| | | | |
|---|---|---|---|
| 4,055,491 A | 10/1977 | Porath-Furedi | |
| 4,158,629 A | 6/1979 | Sawyer | |
| 4,165,273 A | 8/1979 | Azarov et al. | |
| 4,173,725 A | 11/1979 | Asai et al. | |
| 4,204,096 A | 5/1980 | Barcus et al. | |
| 4,398,325 A | 8/1983 | Piaget et al. | |
| 4,666,595 A | 5/1987 | Graham | |
| 4,699,588 A | 10/1987 | Zinn et al. | |
| 4,743,361 A | 5/1988 | Schram | |
| 4,759,775 A | 7/1988 | Peterson et al. | |
| 4,836,684 A * | 6/1989 | Javorik et al. | 366/114 |
| 4,983,189 A * | 1/1991 | Peterson et al. | 210/748.02 |
| 5,164,094 A * | 11/1992 | Stuckart | 210/708 |
| 5,225,089 A | 7/1993 | Benes et al. | |
| 5,371,429 A | 12/1994 | Manna | |
| 5,395,592 A | 3/1995 | Bolleman et al. | |
| 5,431,817 A | 7/1995 | Braatz et al. | |
| 5,443,985 A | 8/1995 | Lu et al. | |
| 5,452,267 A | 9/1995 | Spevak | |
| 5,484,537 A | 1/1996 | Whitworth | |
| 5,527,460 A | 6/1996 | Trampler et al. | |
| 5,560,362 A | 10/1996 | Sliwa, Jr. et al. | |
| 5,594,165 A | 1/1997 | Madanshetty | |
| 5,604,301 A | 2/1997 | Mountford et al. | |
| 5,626,767 A | 5/1997 | Trampler et al. | |
| 5,688,405 A | 11/1997 | Dickinson et al. | |
| 5,711,888 A | 1/1998 | Trampler et al. | |
| 5,831,166 A * | 11/1998 | Kozuka et al. | 73/570 |
| 5,834,871 A * | 11/1998 | Puskas | 310/316.02 |
| 5,902,489 A | 5/1999 | Yasuda et al. | |
| 5,912,182 A | 6/1999 | Coakley et al. | |
| 5,951,456 A | 9/1999 | Scott | |
| 6,090,295 A | 7/2000 | Raghavarao et al. | |
| 6,166,231 A | 12/2000 | Hoeksema | |
| 6,205,848 B1 | 3/2001 | Faber et al. | |
| 6,216,538 B1 | 4/2001 | Yasuda et al. | |
| 6,273,262 B1 * | 8/2001 | Yasuda et al. | 209/1 |
| 6,332,541 B1 | 12/2001 | Coakley et al. | |
| 6,391,653 B1 | 5/2002 | Letcher et al. | |
| 6,487,095 B1 | 11/2002 | Malik et al. | |
| 6,592,821 B1 | 7/2003 | Wada et al. | |
| 6,649,069 B2 | 11/2003 | DeAngelis | |
| 6,763,722 B2 | 7/2004 | Fjield et al. | |
| 6,881,314 B1 | 4/2005 | Wang et al. | |
| 6,929,750 B2 | 8/2005 | Laurell et al. | |
| 6,936,151 B1 * | 8/2005 | Lock et al. | 204/547 |
| 7,010,979 B2 | 3/2006 | Scott | |
| 7,061,163 B2 | 6/2006 | Nagahara et al. | |
| 7,081,192 B1 | 7/2006 | Wang et al. | |
| 7,093,482 B2 | 8/2006 | Berndt | |
| 7,108,137 B2 | 9/2006 | Lal et al. | |
| 7,150,779 B2 | 12/2006 | Meegan, Jr. | |
| 7,186,502 B2 | 3/2007 | Vesey | |
| 7,191,787 B1 | 3/2007 | Redeker et al. | |
| 7,331,233 B2 | 2/2008 | Scott | |
| 7,340,957 B2 | 3/2008 | Kaduchak et al. | |
| 7,373,805 B2 | 5/2008 | Hawkes et al. | |
| 7,541,166 B2 | 6/2009 | Belgrader et al. | |
| 7,601,267 B2 * | 10/2009 | Haake et al. | 210/748.05 |
| 7,673,516 B2 | 3/2010 | Janssen et al. | |
| 7,837,040 B2 | 11/2010 | Ward et al. | |
| 7,846,382 B2 | 12/2010 | Strand et al. | |
| 7,968,049 B2 | 6/2011 | Takahashi et al. | |
| 8,080,202 B2 | 12/2011 | Takahashi et al. | |
| 8,134,705 B2 * | 3/2012 | Kaduchak et al. | 356/337 |
| 8,256,076 B1 | 9/2012 | Feller | |
| 8,266,950 B2 | 9/2012 | Kaduchak et al. | |
| 8,273,253 B2 | 9/2012 | Curran | |
| 8,273,302 B2 | 9/2012 | Takahashi et al. | |
| 8,309,408 B2 | 11/2012 | Ward et al. | |
| 8,319,398 B2 | 11/2012 | Vivek et al. | |
| 8,334,133 B2 | 12/2012 | Fedorov et al. | |
| 8,387,803 B2 | 3/2013 | Thorslund et al. | |
| 8,679,338 B2 | 3/2014 | Rietman et al. | |
| 8,691,145 B2 * | 4/2014 | Dionne et al. | 422/20 |
| 8,873,051 B2 * | 10/2014 | Kaduchak et al. | 356/337 |
| 2002/0134734 A1 | 9/2002 | Campbell et al. | |
| 2003/0195496 A1 | 10/2003 | Maguire | |
| 2003/0209500 A1 | 11/2003 | Kock et al. | |
| 2003/0230535 A1 | 12/2003 | Affeld et al. | |
| 2004/0016699 A1 | 1/2004 | Bayevsky | |
| 2005/0196725 A1 | 9/2005 | Fu | |
| 2006/0037915 A1 | 2/2006 | Strand et al. | |
| 2007/0272618 A1 | 11/2007 | Gou et al. | |
| 2007/0284299 A1 | 12/2007 | Xu et al. | |
| 2008/0217259 A1 | 9/2008 | Siversson | |
| 2009/0029870 A1 | 1/2009 | Ward et al. | |
| 2009/0045107 A1 | 2/2009 | Ward et al. | |
| 2009/0053686 A1 | 2/2009 | Ward et al. | |
| 2009/0098027 A1 | 4/2009 | Tabata et al. | |
| 2009/0178716 A1 | 7/2009 | Kaduchak et al. | |
| 2009/0194420 A1 | 8/2009 | Mariella, Jr. et al. | |
| 2009/0295505 A1 | 12/2009 | Mohammadi et al. | |
| 2010/0000945 A1 | 1/2010 | Gavalas | |
| 2010/0078384 A1 | 4/2010 | Yang | |
| 2010/0124142 A1 | 5/2010 | Laugharn et al. | |
| 2010/0192693 A1 | 8/2010 | Mudge et al. | |
| 2010/0193407 A1 | 8/2010 | Steinberg et al. | |
| 2010/0206818 A1 | 8/2010 | Leong et al. | |
| 2010/0255573 A1 | 10/2010 | Bond et al. | |
| 2010/0317088 A1 | 12/2010 | Radaelli et al. | |
| 2010/0323342 A1 | 12/2010 | Gonzalez Gomez et al. | |
| 2010/0330633 A1 | 12/2010 | Walther et al. | |
| 2011/0024335 A1 | 2/2011 | Ward et al. | |
| 2011/0092726 A1 | 4/2011 | Clarke | |
| 2011/0123392 A1 | 5/2011 | Dionne et al. | |
| 2011/0154890 A1 | 6/2011 | Holm et al. | |
| 2011/0166551 A1 | 7/2011 | Schafer | |
| 2011/0262990 A1 | 10/2011 | Wang et al. | |
| 2011/0281319 A1 | 11/2011 | Swayze et al. | |
| 2011/0309020 A1 | 12/2011 | Rietman et al. | |
| 2012/0088295 A1 | 4/2012 | Yasuda et al. | |
| 2012/0328477 A1 | 12/2012 | Dionne et al. | |
| 2012/0329122 A1 | 12/2012 | Lipkens et al. | |
| 2013/0277316 A1 | 10/2013 | Dutra et al. | |
| 2013/0284271 A1 | 10/2013 | Lipkens et al. | |
| 2014/0011240 A1 | 1/2014 | Lipkens et al. | |

FOREIGN PATENT DOCUMENTS

| | | |
|---|---|---|
| EP | 1 254 669 B1 | 11/2002 |
| GB | 2 420 510 A | 5/2006 |
| WO | WO 87/07178 A1 | 12/1987 |
| WO | WO 02/072234 A1 | 9/2002 |
| WO | WO 2009/111276 A1 | 9/2009 |
| WO | WO-2009111276 | 9/2009 |
| WO | WO 2009/144709 A1 | 12/2009 |
| WO | WO 2010/024753 A1 | 4/2010 |
| WO | WO 2011/023949 A2 | 3/2011 |
| WO | WO 2011/027146 A2 | 3/2011 |
| WO | WO 2011/161463 A2 | 12/2011 |

OTHER PUBLICATIONS

B. Lipkens, J. Dionne, A. Trask, B. Szczur, and E. Rietman, "Prediction and measurement of particle velocities in ultrasonic standing waves," J. Acoust. Soc. Am. 124, No. 4, pp. 2492 (A) 2008.

(56) References Cited

OTHER PUBLICATIONS

B. Lipkens, J. Dionne, M. Costolo, and E. Rietman, "Frequency sweeping and fluid flow effects on particle trajectories in ultrasonic standing waves," Acoustics 08, Paris, Jun. 29-Jul. 4, 2008.

B. Lipkens, M. Costolo, and E. Rietman, "The effect of frequency sweeping and fluid flow on particle trajectories in ultrasonic standing waves", IEEE Sensors Journal, vol. 8, No. 6, pp. 667-677, 2008.

Castro, V.E., "Tunable gap and quantum quench dynamics in bilayer graphene"; Jul. 13, 2010, Mathematica Summer School.

Garcia-Lopez, "Enhanced Acoustic Separation of Oil-Water Emulsion in Resonant Cavities", The Open Acoustics Journal, pp. 66-71, 2008.

L. P. Gor'kov, "On the forces acting on a small particle in an acoustical field in an ideal fluid," Soy. Phys. Dokl., vol. 6, pp. 773-775, 1962.

Meribout, et al., "An Industrial-Prototype Acoustic Array for Real-Time Emulsion Layer Detection in Oil Storage Tanks", IEEE Sensors Journal, vol. 9, No. 12, Dec. 2009.

Pangu, et al., "Droplet transport and coalescne kinetecs in emulsions subjected to acoustic fields", Ultrasonics 46, pp. 289-302 (2007).

Ponomarenko et al. "Density of states and zero Landau level probed through capacitance of graphene"; Nature Nanotechnology Letters; Jul. 5, 2009; DOI: 10.1038/NNANO.2009.177.

Sony News Release: <http://www.sony.net/SonyInfo/News/Press/201010/10-137E/index.html>, (2010).

Alvarez et al.; Shock Waves, vol. 17, No. 6, pp. 441-447, 2008.

Benes et al.; Ultrasonic Separation of Suspended Particles, 2001 IEEE Ultrasonics Symposium; Oct. 7-10, 2001; pp. 649-659; Atlanta, Georgia.

Castro; Tunable gap and quantum quench dynamics in bilayer graphene; Jul. 13, 2010; Mathematica Summer School.

Cravotto et al.; Ultrasonics Sonochemistry, vol. 15, No. 5, pp. 898-902, 2008.

Garcia-Lopez, et al; Enhanced Acoustic Separation of Oil-Water Emulsion in Resonant Cavities. The Open Acoustics Journal. 2008, vol. 1, pp. 66-71.

Hill et al.; Ultrasonic Particle Manipulation; Microfluidic Technologies for Miniaturized Analysis Systems, Jan. 2007, pp. 359-378.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al., Macro-scale acoustophoretic separation of lipid particles from red blood cells, The Journal of the Acoustical Society of America, vol. 133, Jun. 2, 2013, p. 045017, XP055162509, New York, NY.

Meribout et a.; An Industrial-Prototype Acoustic Array for Real-Time Emulsion Layer Detection in Oil Storage Tanks; IEEE Sensors Journal, vol. 9, No. 12, Dec. 2009.

Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).

Ponomarenko et al.; Density of states and zero Landau level probed through capacitance of graphene; Nature Nanotechnology Letters, Jul. 5, 2009; DOI: 10.1038/NNANO.2009.177.

Seymour et al, J. Chem. Edu., 1990, 67(9), p. 763, published Sep. 1990.

Annex to Form PCT/ISA/206—Communication Relating to the Results of the Partial International Search Report, dated Jul. 18, 2013.

European Search Report of European Application No. 11769474.5 Dated Oct. 10, 2012.

International Search Report and Written Opinion dated Dec. 20, 2011, for corresponding PCT application No. PCT/US2011/032181.

International Search Report and Written Opinion dated Feb. 27, 2012, for PCT application No. PCT/US2011/040787.

International Search Report and Written Opinion of International Application No. PCT/US2013/037404 Dated Jun. 21, 2013.

International Search Report and Written Opinion of International Application No. PCT/US2013/050729 Dated Sep. 25, 2013.

International Search Report for corresponding PCT Application Serial No. PCT/US2014/015382 dated May 6, 2014.

Phys. Org. "Engineers develop revolutionary nanotech water desalination membrane." Nov. 6, 2006. http://phys.org/news82047372.html.

"Proceedings of the Acoustics 2012 Nantes Conference," Apr. 23-27, 2012, Nantes, France, pp. 278-282.

Sony New Release: <http://www.sony.net/SonyInfo/News/Press/201010/10-137E/index.html>.

\* cited by examiner

601

ULTRASOUND AND ACOUSTOPHORESIS FOR WATER PURIFICATION

RELATED APPLICATIONS

This application is a divisional of U.S. patent application Ser. No. 12/947,757, filed Nov. 16, 2010, now U.S. Pat. No. 8,691,145, which claimed priority to U.S. Provisional Patent Application No. 61/261,686, filed on Nov. 16, 2009, and U.S. Provisional Patent Application No. 61/261,676, filed on Nov. 16, 2009, all of which are incorporated, herein, by reference in their entireties.

TECHNICAL FIELD

The subject matter described herein relates to the use of ultrasonically generated acoustic standing waves to achieve trapping, concentration, and separation of suspended-phase components and thereby remove such contaminants from a fluid medium such as water.

BACKGROUND

There is great interest and need for water purification for developing countries. The world population is approximately 6.7 billion people and is expected to be over 8 billion by 2050. Roughly 1.1 billion people in the world lack access to safe drinking water. Available water sources can be contaminated by pathogens. Roughly 2.2 million die each year from consumption of pathogen contaminated water and 9500 children die each day.

Most of the work reported in the literature for pathogen removal from water involves replaceable filter units. These units generally consist of packed cartridges, filter membranes, or special filter papers. Though organisms over 10 micron can be easily captured by these techniques, smaller organisms including bacterial spores in the size range of 1 micron are typically not captured with sufficient efficiency.

SUMMARY

The current subject matter provides, among other possible advantages, a solid-state, low-cost alternative to filter cartridges and filter membranes that is capable of processing large quantities of a host medium, for example water, that is laden with microorganisms or other suspended particles. Various implementations of the current subject matter can efficiently trap, concentrate, and separate such microorganisms and particles from the host medium. Systems, methods, and the like according to the current subject matter can rupture the cell walls and cellular membranes of microorganisms and can also concentrate and remove metal, metal oxide, and other types of particles without clogging a filter or a membrane.

Ultrasound waves can also rupture the cellular walls of microorganisms such as *Giardia* (6-10 microns), *Cryptosporium* (4-7 microns) and *Trematodes*. Acoustophoresis can separate smaller microorganisms such as *Lepospira*, and *Salmonella* from water sources for human and livestock consumption. Acoustophoresis can be used to sort particles of different sizes, density, or compressibility in a single pass through an acoustophoretic cavity.

Some implementations of the current subject matter employ in situ electrochemical generation of ozone in conjunction with standing acoustic waves generated by ultrasonic transducers to achieve separation and concentration of secondary-phase and dissolved components from water or other host media. Electrochemically generated ozone can induce precipitation of dissolved metals by formation of metal oxides and also destroy small organisms, such as for example viruses, bacteria spores, and the like. Additionally, reactions of ozone with dissolved organic compounds can reduce or eliminate toxicity of these compounds. In some cases, the resulting products of such reactions can be less soluble or less chemically stable in water. Ozone can also enhance destruction of small organisms in the size range from 10 nm to about 1-2 microns. When used in conjunction with the elevated pressures created at nodes of an acoustic standing wave, ozone solubility in the fluid medium (for example water) can be increased. This increased solubility of ozone creates an increased concentration of ozone in the fluid phase, which can enhance destruction of organic compounds and microorganisms and also speed up oxidation of dissolved metals to form less soluble chemical species that are more readily removed from the fluid medium.

Ozone can be produced directly in water, for example by electrochemical generation. The technique can involve lead oxide as a catalytic surface, an acidic or perfluorinated electrolyte, and a platinum counter electrode. In this technique, as little as 2-3 volts can be required. A perfluorinated polymeric electrolyte and non-toxic electrodes such as platinum black, inert noble metals, and glassy carbon electrodes are some non-toxic approaches to ozone generation in an acoustic resonator where the ozone is used for its ability to precipitate dissolved metals, destroy small organisms and destroy dissolved organics. Precipitated substances can be collected in an acoustic standing wave where the acoustic standing wave also crushes larger organisms (10-1000 microns).

Other advantages of the current subject matter can include, but are not limited to, use of acoustophoresis for separations in extremely high volumes and in flowing systems with very high flow rates. Micron-size particles, for which the acoustophoretic force is quite small, can nonetheless be agglomerated into larger particles that are readily removed by gravitational settling. For example, *Bacillus cereus* bacterial spores (a model for anthrax) can be trapped in an acoustophoretic cavity embedded in a flow system that can process drinking water at rates up to 120 mL/minute (1 cm/second linear flow). Concentration ratios of 1000 or more are possible using a single-pass acoustocollector. Other, larger fluid flow rates are possible using larger scale flow chambers.

More specifically, the current subject matter describes an apparatus including a flow chamber with an inlet and an outlet through which is flowed a mixture of a fluid and a particulate and two or more ultrasonic transducers embedded in or outside of a wall of said flow chamber. When the two or more ultrasonic transducers are located outside the flow chamber wall the thickness of the flow chamber wall can be tuned to maximize acoustic energy transfer into the fluid. The ultrasonic transducers are arranged at different distances from the inlet of the flow chamber. The ultrasonic transducers can be driven by an oscillating, periodic, or pulsed voltage signal of ultrasonic frequencies. The apparatus also includes two or more reflectors corresponding to each ultrasonic transducer located on the opposite wall of the flow chamber from to the corresponding transducer. Each ultrasonic transducer forms a standing acoustic wave at a different ultrasonic frequency. Each frequency can be optimized for a specific range of particle sizes in the fluid.

The fluid can be flowed horizontally through the flow chamber. The fluid can be water. The particulate can be selected from microalgae, yeast, fungi, bacteria, spores, gases or oils, metal oxides, metal particles, clays, dirt, plastics, or any particulate with a non-zero contrast factor. The oscillating, periodic, or pulsed voltage signal of ultrasonic frequencies can be in the range of 10 kHz to 100 MHz.

The apparatus can contain three, four, five, or more ultrasonic transducers. Each transducer forms a standing acoustic wave at a different ultrasonic frequency and each frequency can be optimized for a specific range of particle sizes in the fluid.

The apparatus can be used to produce two or more acoustic standing waves in the fluid. The standing waves can be perpendicular to the direction of the mean flow in the flow channel. The standing waves can have a horizontal or vertical orientation. The standing waves can then exert acoustic radiation force on the particulate, such that the particulate is trapped in the acoustic field against the fluid drag force. Thus, the particulate is concentrated in the acoustic field over time. The frequency of excitation of the standing waves can be constant or be varied in a sweep pattern. The sweep pattern variation can be used to translate the collected particles along the direction of the acoustic standing waves to either the transducer face or to the reflector face.

The apparatus can also include a collection pocket positioned on the transducer or on the wall of the flow chamber opposite of the transducer. The pocket can be planar, conical, curved, or spherical in shape.

The ultrasonic transducer can be made of a piezo-electric material.

The apparatus can also include an additional one or more transducers embedded in the flow channel wall or outside of the vessel wall, with the wall thickness tuned to maximize acoustic energy transfer. For each transducer a reflector is positioned on the opposite wall of the flow chamber. The collection pocket can also have a first door that seals the pocket away from the fluid. The collection pocket can also be connected to a conduit. This conduit can include a second door which prevents entry of fluid from the flow chamber into the conduit when the first door is open.

The apparatus can also include a device that electrochemically generates ozone. The device can be an electrochemical sandwich system for generating ozone underwater comprising a layer of platinum mesh, over a layer of platinum black, over a layer of Nafion® (tetrafluoroethylene-perfluoro-3,6-dioxa-4-methyl-7-octenesulfonic acid copolymer), over a layer of graphite, over a layer of platinum mesh. The layers are held together with nylon screws and nuts. The system can be operated at between 1 and 100 volts (DC). The system can also be used to induce the precipitation of dissolved metals and to react the ozone with metal ions to produce metal oxides in water. Also, the system can be used to kill, through oxidation, suspended virus particles, bacterial spores, and microorganisms in the size range of 1 micron to 100 microns.

The current subject matter also describes a method of separating particulate from a fluid comprising flowing the fluid past two or more positions; and forming acoustic standing waves at the two or more positions. Each standing acoustic wave can be maintained at a different ultrasonic frequency and each ultrasonic frequency can be optimized for a specific range of particle sizes. The particulate of the optimized size is trapped in its corresponding acoustic standing wave against the flow of the fluid. Thus, the particulate is concentrated in its corresponding acoustic standing wave.

This method can further include sweeping the frequency of the acoustic standing wave thereby directing the concentrated particulate into a collection pocket. The two or more acoustic standing wave can be a pulsed waveform resulting in high intensity acoustic pressure. The high intensity acoustic pressure can have sufficient amplitude to rupture the cell wall and cellular membranes of microorganisms.

The method can also include the electrochemical generation of ozone. The ozone can be generated in sufficient quantity to destroy dissolved metals, dissolved organics, and submicron organisms and collection of precipitated metal oxides and microorganisms in the size range of 1-100 microns.

The ozone can be produced by an electrochemical sandwich system for generating ozone underwater comprising a layer of platinum mesh, over a layer of platinum black, over a layer of Nafion®, over a layer of graphite, over a layer of platinum mesh. The layers can be held together with nylon screws and nuts. The system can be operated at between 1 and 100 volts (DC). The system can also be used to induce the precipitation of dissolved metals and react the ozone with metal ions to produce metal oxides in water. The system can also be used to kill, through oxidation, suspended virus particles, bacterial spores, and microorganisms in the size range of 1 micron to 100 micron.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations.

DETAILED DESCRIPTION

An acoustophoretic separator can be created in some implementations using a piezoelectric acoustic transducer and an opposing reflection surface (or a second transducer) to set up a resonant standing wave in the fluid of interest. The ultrasonic standing waves create localized regions of high and low pressure, corresponding to high and low density of the fluid. Secondary phase contaminants are pushed to the standing wave nodes or antinodes depending on their compressibility and density relative to the surrounding fluid. Particles of higher density and compressibility (e.g., bacterial spores) move to the nodes in the standing waves while secondary phases of lower density (such as oils) move to the antinodes. The force exerted on the particles also depends on their size, with larger particles experiencing larger forces.

The acoustic radiation force ($F_{ac}$) acts on the secondary-phase particles (or organisms), pushing them to the nodes (or antinodes) of the acoustic standing wave. The magnitude of the force depends on the particle density and compressibility relative to the fluid medium, and increases with the particle volume.

Figure 2:
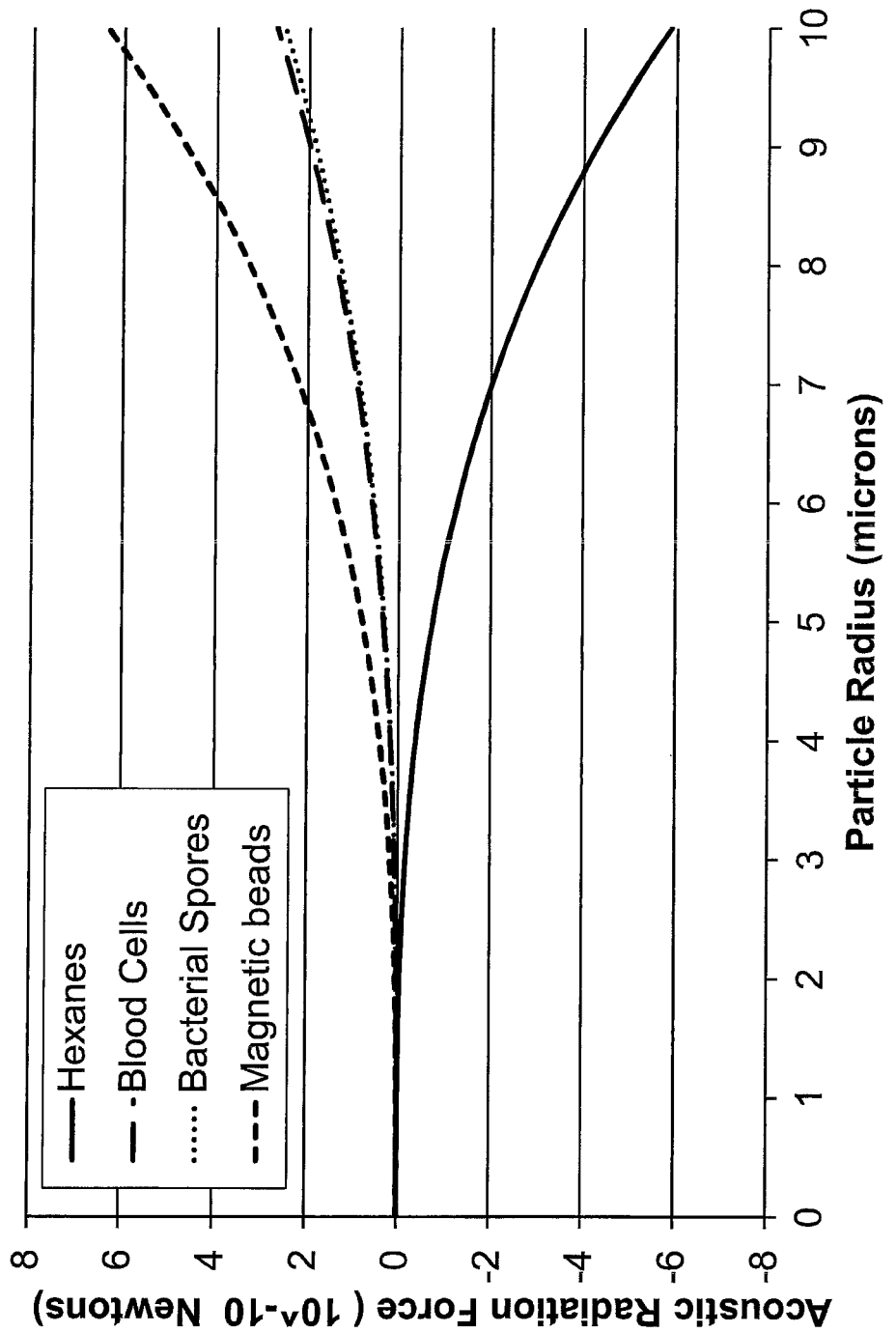
FIG. 2 shows a graph showing acoustic force operating on micron-size particles as a function of the particle (or droplet) radius at a frequency of 1 MHz and an acoustic pressure amplitude of 0.5 MPa.

Besides microorganisms, the acoustic pressures of the standing wave can also separate low-density droplets and higher density particles, such as metal oxides (in the size range of 0.2 microns to 100 microns). FIG. 2 shows a chart illustrating the acoustic force that operates on four different secondary phases in water as a function of the particle (or droplet) radius. The four secondary phases are hexanes (a mixture of hydrocarbons, a model for oils, represented by line at the top of the graph), red blood cells (a model for biological cells) and bacterial spores both of which are represented by the lines in the center of the graph, and paramagnetic polystyrene beads (examples of particles with density and size similar to metal oxide particles represented by the line at the bottom of the graph). The forces for an applied acoustic frequency of 1 MHz (typical for an ultrasonic transducer) and an acoustic pressure of 0.5 MPa maximum at the antinodes (readily achieved in water) are shown in FIG. 2. For microorganisms in the range of 3-10 microns, the acoustic force can crush/rupture their cell walls. Larger organisms in the range of 10-100 microns can experience organ failure and thus organism death as a result of the acoustic pressure. Achievement of higher applied acoustic frequencies and higher acoustic pressures can afford better separation of smaller metal oxide particles as well as particles of other compositions, for example those on the order of 10 nm in diameter.

An ultrasonic transducer operating at a fixed frequency f (Hz) can create an acoustic standing wave in a fluid-filled cavity. The standing wave can be characterized by a local pressure p that is a function of position (x) and time (t), $$p(x,t) = P\cos(kx)\sin(\omega t), \quad (1)$$

where P is the amplitude of the acoustic pressure; k is the wave number (equal to $2\pi/\lambda$, where $\lambda$ is the wavelength), and $\omega = 2\pi f$, where $\omega$ is the angular frequency. The pressure of the acoustic wave produces an acoustic radiation force $F_{ac}$ on secondary-phase elements according to $$F_{ac} = X\pi R_p^3 k \frac{P^2}{\rho_f c_f^2}\sin(2kx), \quad (2)$$

where $R_p$ is the particle radius, $\rho_f$ is the density of the fluid medium, $c_f$ is the speed of sound in the fluid, and X is the acoustic contrast factor, defined by $$X = \frac{1}{3}\left[\frac{5\Lambda}{1+2\Lambda} - \frac{1}{\sigma^2\Lambda}\right], \quad (3)$$

where $\Lambda$ is the ratio of the particle density to fluid density and .sigma. is the ratio of the speed of sound in the particle to the sound speed in the fluid. The acoustic radiation force acts in the direction of the acoustic field and is proportional to the product of acoustic pressure and acoustic pressure gradient. An inspection of the acoustic radiation force shows that it is proportional to the particle volume, frequency (or wave number), the acoustic energy density (or the square of the acoustic pressure amplitude), and the acoustic contrast factor. The spatial dependency has twice the periodicity of the acoustic field. The acoustic radiation force is thus a function of two mechanical properties: density and compressibility. Examples are shown in Table 1.

TABLE 1

Properties of water and 4 selected secondary phases

| Material | ρ (density) (kg/m³) | c (speed of sound in the medium) (m/s) | Λ (dimensionless) | X (dimensionless) |
|---|---|---|---|---|
| Water | 1000 | 1509 | — | — |
| Hexanes | 720 | 1303 | 0.72 | −0.402 |
| Blood Cells | 1125 | 1900 | 1.125 | 0.185 |
| Bacterial Spores | 1100 | 1900 | 1.1 | 0.173 |
| Magnetic beads | 2000 | 1971 | 2 | 0.436 |

For three dimensional acoustic fields, a more general approach for calculating the acoustic radiation force is needed. Gor'kov's formulation can be used for this [5]. Gor'kov developed an expression for the acoustic radiation force $F_{ac}$ applicable to any sound field. The primary acoustic radiation force is defined as a function of a field potential U, given by $$F_{ac} = -\nabla(U) \quad (4)$$

where the field potential U is defined as $$U = V_0\left[\frac{\langle p^2(x,y,t)\rangle}{2\rho_f c_f^2}f_1 - \frac{3\rho_f\langle v^2(x,y,t)\rangle}{4}f_2\right] \quad (5)$$

and $f_1$ and $f_2$ are the monopole and dipole contributions defined by $$f_1 = 1 - \frac{1}{\Lambda\sigma^2}, \quad (6)$$

$$f_2 = \frac{2(\Lambda-1)}{2\Lambda+1},$$

where p(x,y,z,t) is the acoustic pressure and v(x,y,z,t) is the fluid particle velocity. $V_o$ is the volume of the particle.

In one implementation that can be used to concentrate and separate microorganisms from water, a flow channel can be used to direct flow of fluid dispersion, typically water and a secondary-phase component that is dispersed in the water. The secondary-phase component in one example can include microorganisms of interest, such as for example *Giardia* (6-10 microns), *Cryptosporium* (4-7 microns) *Trematodes* (egg and larval stages are microscopic), *Lepospira* (6-20 microns), and *Salmonella* (0.7-1.5 microns). A microorganism of interest can have an average diameter between 0.5 and 100 microns. A microorganism of interest can also have an average diameter between 0.5 and 20 microns. A microorganism of interest can also have an average diameter between 0.5 and 10 microns. An ultrasonic transducer, which in some implementations can be a piezoelectric transducer, can be located in the wall of the flow channel. The transducer can be driven by an oscillating voltage that has an oscillation at an ultrasonic frequency that can in some implementations be in a range of several Megahertz. The voltage amplitude can be between 1 and 100 volts. The transducer, in combination with an acoustic reflection surface located at the wall of the flow tube opposite to the transducer, can generate an acoustic standing wave across the flow channel. Typical pressure amplitudes in the region of the acoustic standing wave or field can be on the order of 0.5 MPa. Such amplitudes are readily available with piezoelectric transducers. This pressure can be high enough to crush and destroy organisms above 10 microns.

FIG. 3 is a set of photographs showing acoustophoretic collection of algae (similar size, density and Young's Modulus as microorganisms such as *Giardia* and *Cryptosporium*) in a flowing water stream. A flat, circular transducer was used in the acoustocollector of FIG. 3. The pressure field of this transducer is a Bessel function for the radial component in addition to the linear standing wave. The radial component acts to hold the captured microorganisms in a column [301, 302] against the fluid flow. The trapped microorganisms or particles can then be further concentrated by gravitational settling or by being driven to a collector pocket through a slow frequency sweeping method. The collection pocket does not have to be planar, it can also be shaped, conical, curved or spherical. The transducer is at the top, just out of the image in FIG. 3. The column of trapped algae [302] is about 2.5 cm high×1 cm wide. The ultrasonic pressure nodes can be seen as the horizontal planes in which the algal cells are captured. The water flow is from left to right. *D. salina* is the same size/density range as many pathogens.

The pressure amplitudes for this acoustophoresis process can, in some implementations, advantageously be maintained below the cavitation threshold values so that a high intensity standing wave field can be created without generation of cavitation effect or significant acoustic streaming. Acoustic streaming refers to a time-averaged flow of the water produced by the sound field. Typically, when acoustic streaming is generated it results in circulatory motion that can cause stirring in the water. Cavitation typically occurs when there are gas bodies, such as air microbubbles, present in the water. The effect of the sound pressure is to create microbubble oscillations which lead to microstreaming and radiation forces. Micro-streaming around bubbles lead to shearing flow in the surrounding liquid. This flow contains significant velocity gradients. If a microorganism is located in this shearing flow, the uneven distribution of forces on the cell walls can lead to significant shear stresses exerted on the cell walls that may lead to cell wall disruption and rupture. At higher sound intensity levels, the microbubble oscillations can become more intense, and the bubble can collapse leading to shock wave generation and free radical production. This is termed inertial cavitation. In some alternative implementations, a pre-treatment step in which cavitation is induced can be used to damage or at least partially destroy suspended biological contaminants. Following a region of the flow path where cavitation is induced, acoustophoresis as described herein can be used to agglomerate suspended material and also to cause damage to smaller suspended pathogens that might not be affects by the larger scale forces of a cavitation environment.

The acoustophoretic force created by the acoustic standing wave on the secondary phase component, such as for example the microorganisms or particles, can be sufficient to overcome the fluid drag force exerted by the moving fluid on these particles. In other words, the acoustophoretic force can act as a mechanism that traps the microorganisms in the acoustic field. The acoustophoretic force can drive microorganisms and suspended particles to the stable locations of minimum acoustophoretic force amplitudes. These locations of minimum acoustophoretic force amplitudes can be the nodes of a standing acoustic wave. Over time, the collection of microorganisms at the nodes grows steadily. Within some period of time, which can be minutes or less depending on the concentration of the secondary phase component, the collection of microorganisms can assume the shape of a beam-like collection of microorganisms with disk-shaped collections of microorganisms. Each disk can be spaced by a half wavelength of the acoustic field. The beam of disk-shaped collections of microorganisms can be "stacked" between the transducer and the opposing, acoustically-reflective flow-tube wall, as shown as [501] in FIG. 5. In this manner, acoustophoretic forces can trap and concentrate microorganisms in the region of the acoustic field while the host medium continues to flow past the concentrated microorganisms.

The process of collecting microorganisms can continue until very large volumes of the host medium have flowed through the trapping region and the capture of the containing microorganisms has been attained. Further separation of the concentrated microorganisms from the host medium can be achieved by one or more methods. For a horizontal flow of the host medium, gravitational settling can be used to drive the concentrated microorganisms into collector pockets, demonstrated in FIG. 4 if the microorganisms have a greater density than the host fluid [401, 402 and 403]. If the microorganisms are less dense than the host fluid, the concentrated microorganisms will gain buoyancy and float. For vertical or horizontal flow of the host medium, a slow frequency sweeping method can be used to translate the microorganisms into collector pockets. In this method, the frequency of the acoustic standing wave can be slowly swept over a small frequency range spanning at least a range of two times the frequency corresponding to the lowest-order standing wave mode of the cavity. The sweep period can be, in one example, on the order of one second. This frequency sweeping method can slowly translate the collected microorganisms in the direction of the acoustic field towards one of the walls of the flow chamber where the microorganism can be collected for further processing. This sweep is illustrated in FIG. 8.

In an alternative implementation, the piezoelectric transducer can be driven by a pulsed voltage signal that includes short-duration, large, positive-amplitude voltage spikes, followed by a longer duration of no applied voltage signal. This pulsed pattern can be repeated according to a repetition rate or period. This excitation can generate very large amplitude compressive pressure pulses in water that can be sufficient to rupture the cell walls and cellular membranes of microorganisms prior to acoustophoresis collection.

In another implementation, a piezoelectric transducer can be driven by a pulsed voltage signal that includes short-duration, large, negative-amplitude voltage spikes, followed by a longer duration of no applied voltage signal. This pulsed pattern can be repeated according to a repetition rate or period. This excitation can generate very large amplitude expansion-type pressure pulses in water that can be sufficient to rupture the cell walls and cellular membranes of microorganisms prior to acoustophoresis collection.

The current subject matter can provide large-scale acoustophoretic technology to collect and process microorganism contaminated water to reduce or eliminate pathogens in the water. In an implementation, this effect can be accomplished using a simple one-step process involving acoustophoresis which simultaneously ruptures large (>10 micron) organisms and collects smaller organisms (<10 microns) and suspended particles to acoustic pressure nodes where they accumulate and agglomerate such that gravitational or other processes can effectively remove finally dropping into a collection port for removal. The process can be applied in either batch or continuous flow reactor configurations. The current subject matter can also be used to collect, remove, etc. metal oxides and metal particles form water to purify water, for example drinking water. Both the inorganic particles and the microorganisms can be simultaneously collected in a filter free process.

Figure 1:
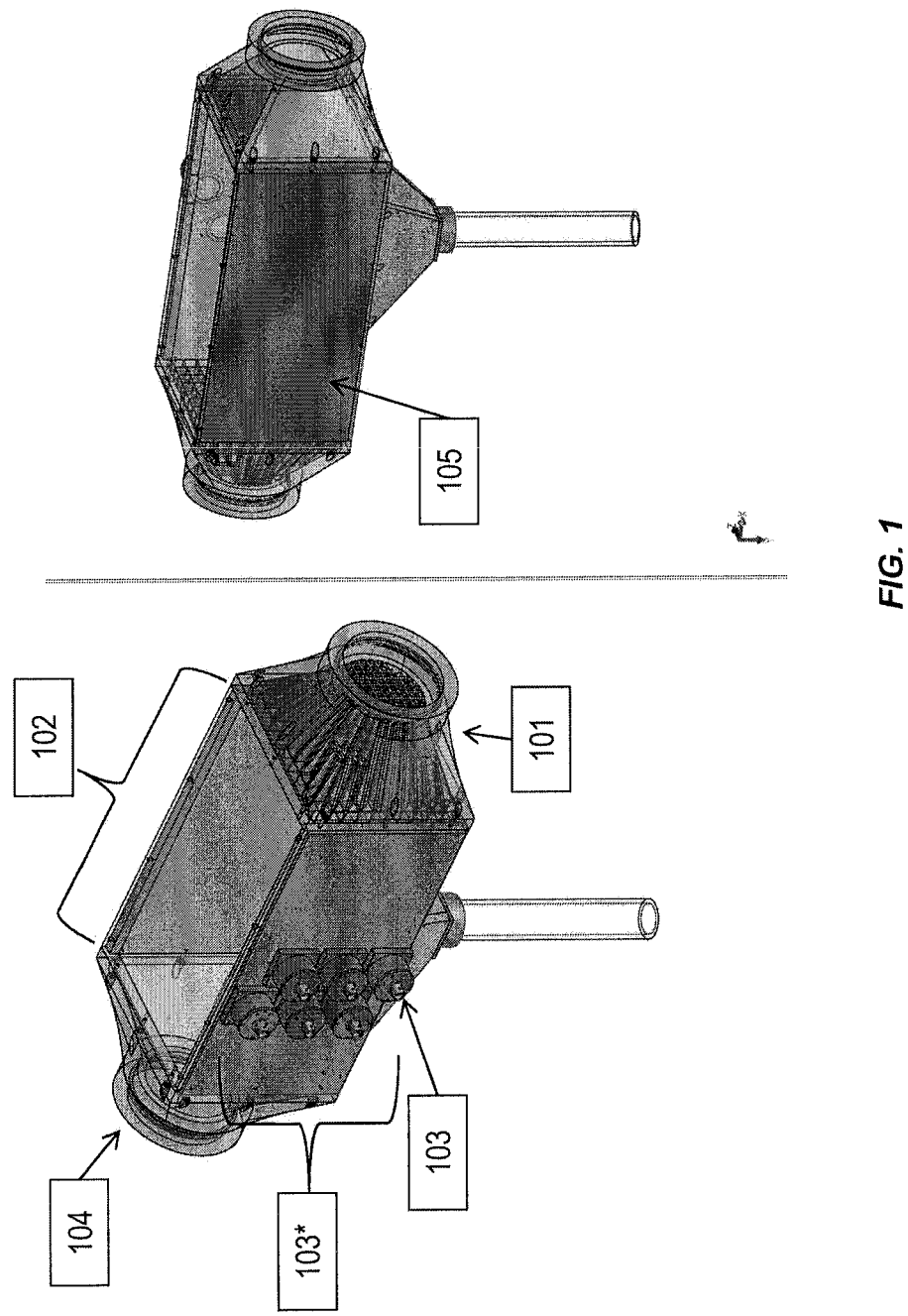
FIG. 1 shows a schematic showing an apparatus that includes showing flow channels, acoustic transducer, reflective surface, and a collection pocket, for the harvesting of microalgae (similar to other microorganisms) and/or dirt particles through acoustophoretic trapping.

In one implementation, a system such as that shown in FIG. 1 for concentrating and separating microorganisms from a host medium such as water can include a flow chamber with an inlet [101] and outlet [104]. The flow direction can in some variations be oriented in a horizontal direction. The flow chamber can receive a mixture of water including a suspended phase that can include microorganisms, such as microalgae, yeast, fungi, bacteria, or spores as well as other, non-biological particles (e.g. metal oxides, clay, dirt, etc.). The flow chamber can have macro-scale dimensions. In other words, the dimensions of the cross-section of the flow chamber are much larger than the wavelength corresponding to the generated sound. The system also includes an ultrasonic transducer [3], that can be embedded in a wall of the flow chamber or located outside of the flow chamber. The ultrasonic transducer can include a piezo-electric material and can be driven by an oscillating voltage signal of ultrasonic frequencies. Ultrasonic transducers other than piezoelectric transducers can be used.

The ultrasonic frequencies can be in the range from 1 kHz to 100 MHz, with amplitudes of 1-100 of volts, normally acting in the tens of volts. The ultrasonic frequencies can be between 200 kHz and 3 MHz. The ultrasonic frequencies can be between 1 and 3 MHz. The ultrasonic frequencies can be 200, 400, 800, 1000 or 1200 kHz. The ultrasonic frequencies can be between 1 and 5 MHz. A reflector [105] can be located opposite to the transducer, such that an acoustic standing wave is generated in the host medium. The acoustic standing wave can be oriented perpendicularly to the direction of the mean flow in the flow channel. In some implementations, the acoustic standing wave can be oriented vertically for a horizontal fluid flow direction. The acoustic field exerts an acoustic radiation force, which can be referred to as an acoustophoretic force, on the suspended phase component. The suspended phase can be trapped in the acoustic field against the fluid drag force, thereby resulting in large scale collection of the suspended phase component. Switching off the water flow through the flow chamber can result in gravitational settling of the collected particles to the bottom of the flow chamber.

Figure 4:
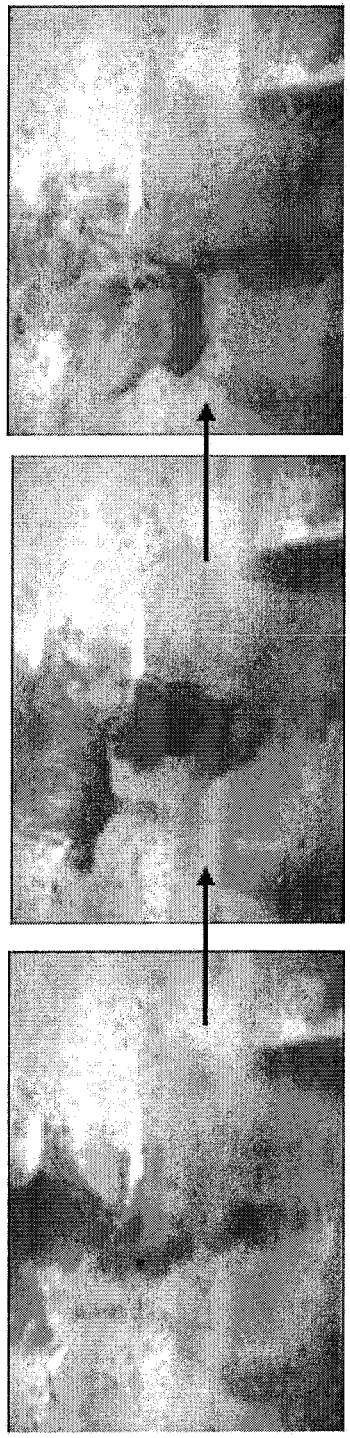
FIG. 4 shows a series of three photos (at 10× magnification) taken at one second intervals to show gravitational settling of microalgae after fluid flow has been stopped and the acoustic field has been turned off.
Figure 5:
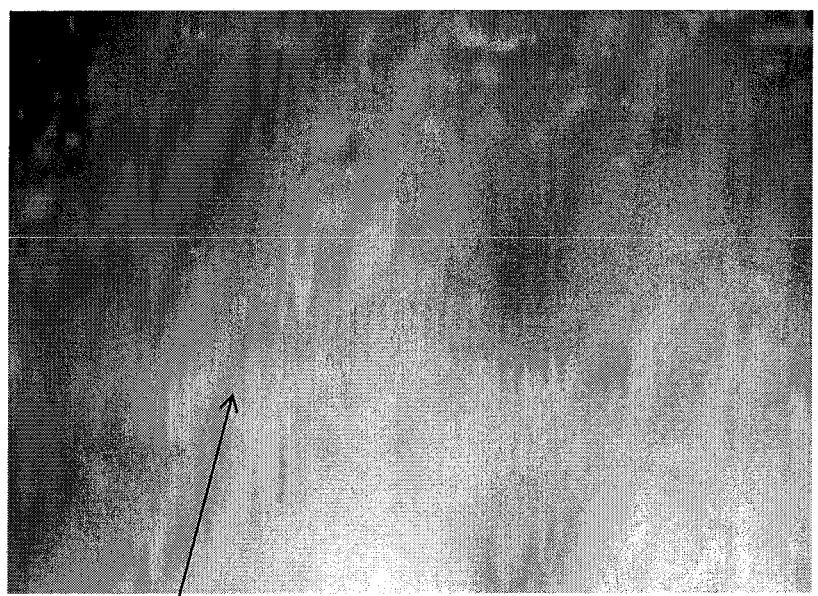
FIG. 5 shows a 10× magnification photograph showing collection of bacterial spore, *B. cerius*, [501] from flowing water in an acoustic chamber.
Figure 8:
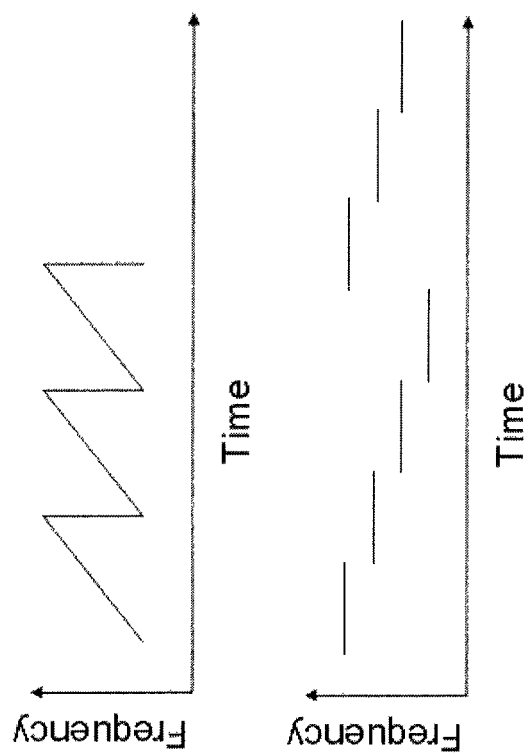
FIG. 8 shows a graph illustrating a frequency sweep used to translate trapped particles along the direction of an acoustic field.

In optional variations, the system can be driven at a constant frequency of excitation and/or with a frequency sweep pattern or step pattern, as shown in FIG. 8. The effect of the frequency sweeping or stepping can be to translate the collected particles along the direction of the acoustic standing wave to either the transducer face or to the opposite reflector face. A collection pocket or other void volume can be positioned opposite to the transducer such that settled particles are collected in the collection pocket, for example as shown in the set of images in FIG. 4. The collection pocket can include one or more butterfly valves or other mechanisms for removing a slurry containing water with a high suspended phase concentration from the flow chamber. In this manner, after the suspended phase settles into the collection pocket, the settled suspended materials are removed from the flowing water stream.

Figure 9:
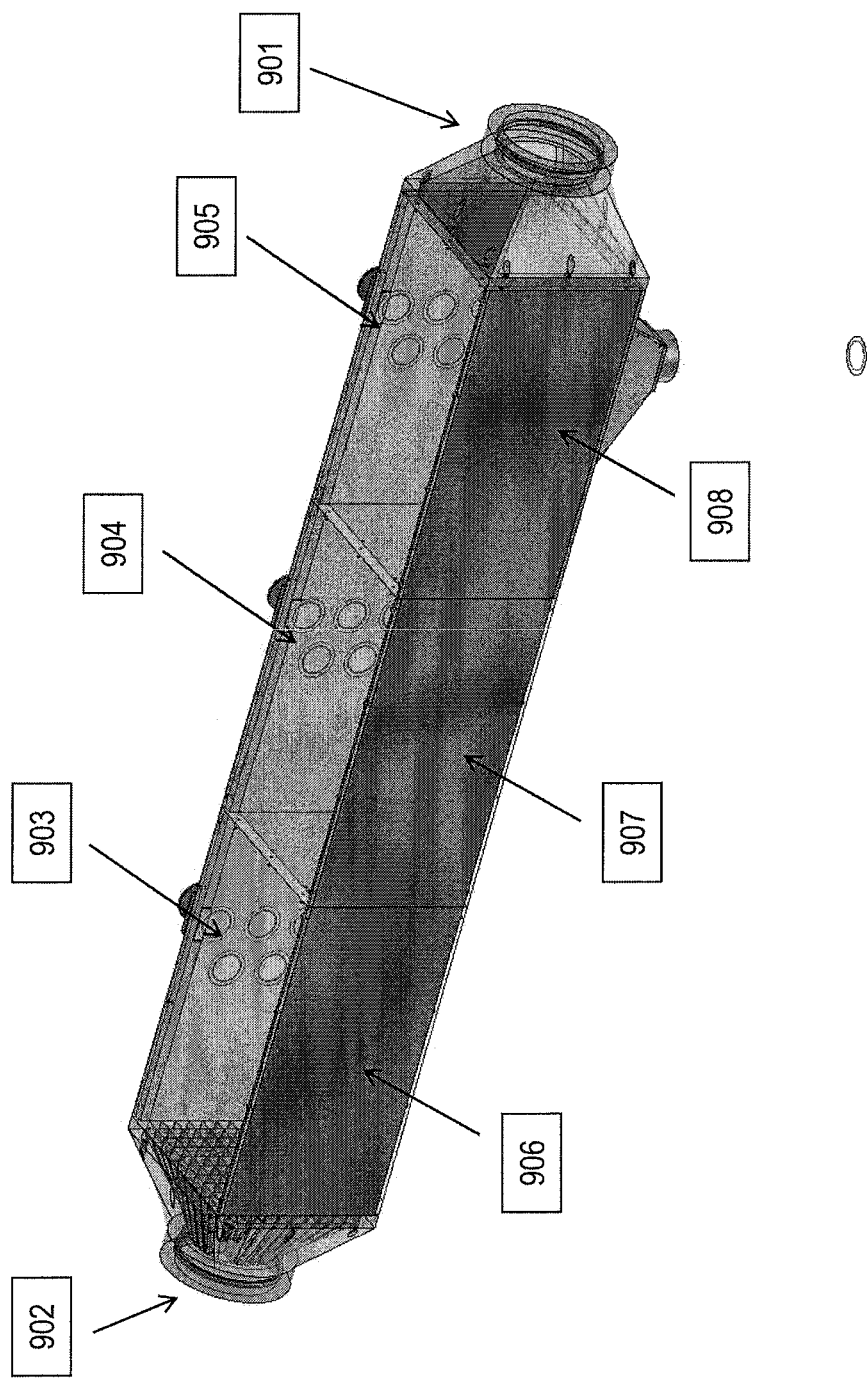
FIG. 9 shows a perspective diagram of an apparatus for trapping, concentration, collection, etc. of microorganisms and inorganic particles and their separation from the host medium, containing multiple systems in line.

The flow direction of a system can be oriented in a direction other than horizontal. For example, the fluid flow can be vertical either upward or downward or at some angle relative to vertical or horizontal. The position of the acoustic transducer can be chosen so that the acoustic field is in a direction such that the translation of particles into a collection pocket can be achieved by a frequency sweeping or stepping method. More than one transducer can be included in the system. For example, as shown in FIG. 9, each transducer can have its own reflector and can include a collector pocket that can further include a mechanism for removing concentrated slurry of suspended phase material from the water flow. A set systems, as shown in FIG. 9, can have each system's transducer set at different frequencies can be used to efficiently concentrate and/or remove suspended material such as metal oxide particles and similar density particles having a range of sizes and densities from a flowing liquid medium.

Figure 7:
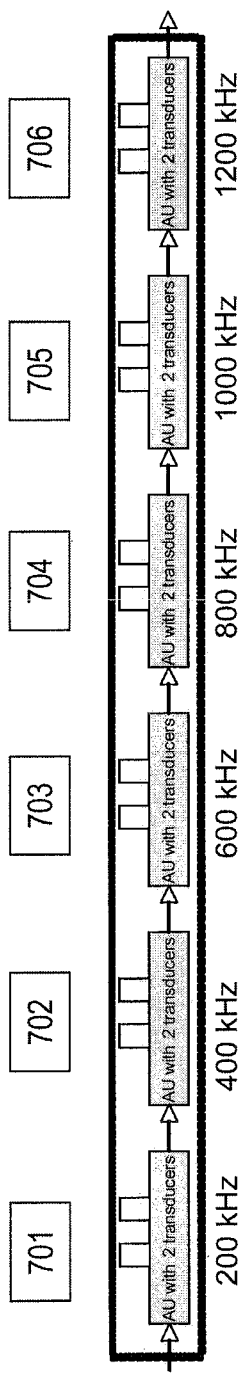
FIG. 7 shows a schematic diagram of a system of acoustophoresis cells operating at different frequencies for removal of particles of different sizes and densities.

Acoustic systems such as that shown in FIG. 1 can also be serially connected with different resonant transducers for greater particle/organism capture efficiency. A schematic diagram of such an implementation is shown in FIG. 7 and FIG. 9. The system can include a series of individual units similar to those shown in FIG. 1. The system shown in FIG. 1 has been optimized to capture of metal oxide particles (as well as particles of other compositions) in the size range of 0.2 to 100 microns and to capture/destroy microorganisms in the size range of 1 to 150 microns. Individual transducers or arrays of transducers are tuned to allow different acoustic frequencies to capture different ranges of particle/organism sizes.

The system of FIG. 7 includes cells operating at 200 kHz [701], 400 kHz [702], 600 kHz [703], 800 kHz [704], 1000 kHz [705] and 1200 kHz [706]. Each cell has been optimized for a specific range of particle/organism size. The overall system as shown in FIG. 1 is capable of processing 1 gal/min of water. Parallel or serial arrays similar to that shown can be constructed to process a variety of volumetric flow rates.

FIG. 9 shows a schematic with three transducers [903, 904, 905] on the wall of a flow chamber with an inlet [902] and an outlet [901]. Each transducer has a corresponding reflector [906, 907 908] on the opposite wall of the flow chamber.

Various implementations of the current subject matter relate to the use of electrochemical generation of ozone under water in conjunction with an acoustophoretic process to precipitate and remove dissolved metals and destroy organisms and dissolved organics and suspended or particulate phase materials. Acoustophoresis can be induced by a standing acoustic wave created ultrasonically. Production of ozone in situ can induce precipitation of dissolved contaminants, for example metal oxides, as well as partial or complete destruction of dissolved organic compounds.

Figure 10:
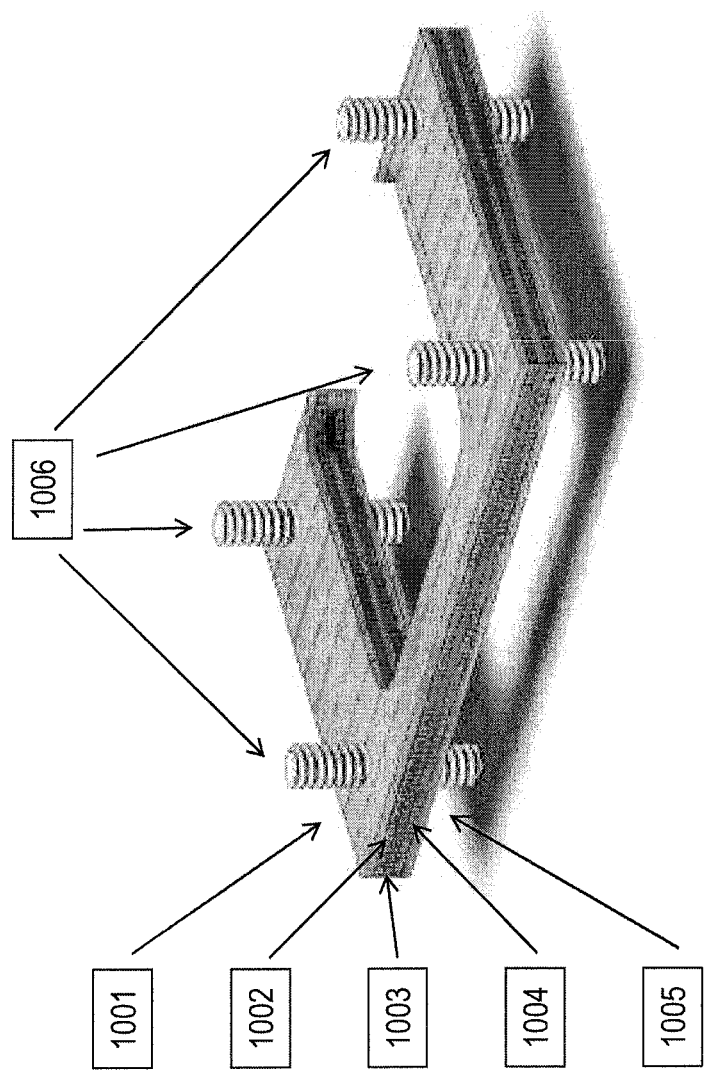
FIG. 10 shows a schematic diagram of an electrochemical sandwich structure used to generate ozone that can be inserted in an acoustic resonance chamber.
Figure 11:
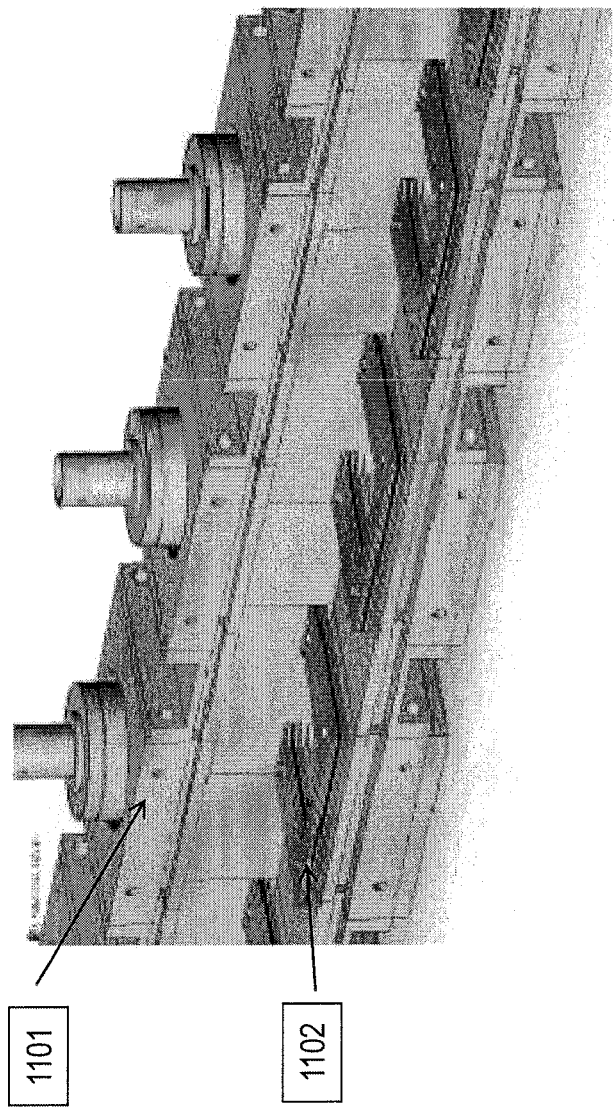
FIG. 11 shows a schematic diagram of an electrochemical cell inside an acoustic chamber.

An electrochemical sandwich system that includes a layer of platinum mesh (contact), platinum black (anode), Nafion® (electrolyte), graphite (cathode), and platinum mesh (contact) held together with nylon screws and nuts can be used in the acoustophoretic cell to generate ozone underwater. Other possible electrodes can include, but are not limited to, stainless steel, noble metals, Ta, Hf, Nb, Au, Ir, Ni, Pt/W alloy, lead oxide, or oxides of titanium. FIG. 10 shows a schematic diagram of an ozone generator that can be used in conjunction with implementations of the current subject matter. A five layer "sandwich" type construction can be used that includes platinum mesh [1001], platinum black, anode, 3) Nafion® (tetrafluoroethylene-perfluoro-3,6-dioxa-4-methyl-7-octenesulfonic acid copolymer) [1003], 4) carbon black, cathode, and 5) platinum mesh [1005]. The layers are held together with nylons screws [1006]. A device such as this can be positioned in the bottom of an acoustic resonator as shown in the schematic diagram of FIG. 11.

In some implementations, ozone can be produced by electrochemical means in an acoustic resonance chamber where water is flowing. The ozone can destroy, through oxidation, dissolved metals, dissolved organics, submicron organisms, and the like. The acoustic field can concentrate and separate microorganisms and other suspended particulate matter from water.

Aspects of the current subject matter described may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

EXAMPLES

Example 1

Separation of Algae from Water Using an Acoustic Standing Wave

In an illustrative implementation, microorganisms including microalgae and bacterial spores were removed from a flowing water stream. As a demonstration of the current subject matter, algae of the halophilic *Dunaliella Salina* (similar in size and density to many pathogenic organisms) were grown in a bottle filled with salt water and placed under a grow light. The algae are removed from the bottle through tubes that pass them into a flow channel and past an acoustic transducer. The apparatus is shown in FIG. 1. The flow chamber was horizontal with the transducer on top facing downward. This resulted in a vertically oriented acoustic standing wave. The transducer used in the system of FIG. 1 is a PZT-4 2 MHZ transducer. Other transducers can be used.

Figure 3:
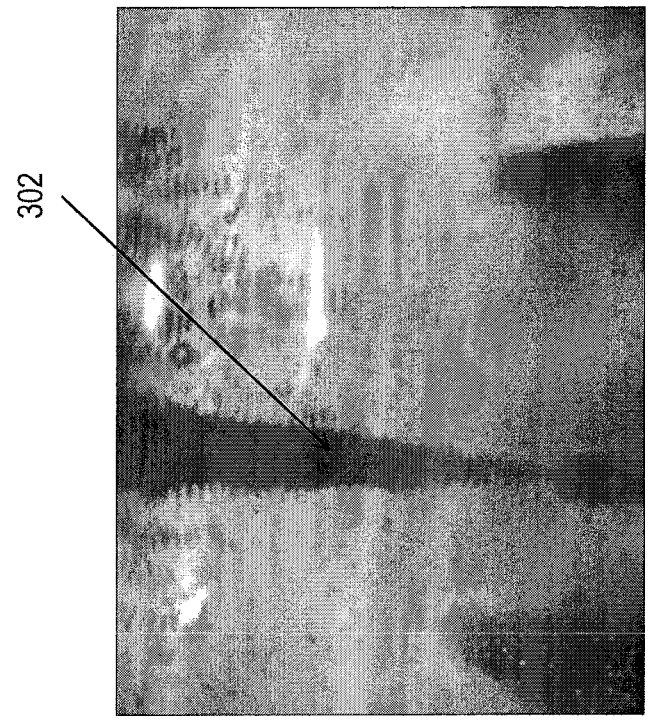
FIG. 3 shows a set of photomicrograph of acoustophoretic trapping of the algae *Dunaliella salina* in flowing water.
Figure 3:
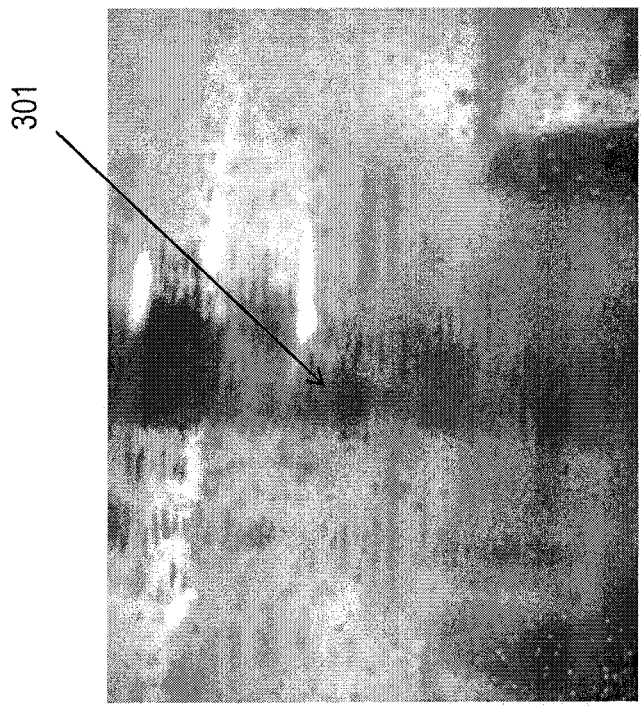

The acoustic transducer was connected to an amplifier which receives its signal from a function generator and operates at about 15 $V_{rms}$ in the current example. Once the fluid flow and the acoustic transducer were turned on, trapping and concentration of microalgae and other particles started quickly. The microalgae and/or particles were trapped in the acoustic field against the fluid drag force by means of the action of the acoustic radiation force. The collection of microalgae and/or particles continued over time and eventually, typically after several minutes, large, beam-like collections of microalgae and/or particles can be seen in the region between the transducer face and the opposition reflective wall. A typical result of the acoustic trapping of microalgae and/or particles for about 3 to 5 minutes in the apparatus of FIG. 1, is shown in the photomicrograph of FIG. 3.

Example 2

Breaking Cell Wall and Cell Membranes of Microorganisms Using an Acoustic Standing Wave Ultrasonic cavitation can be used to crush larger organisms (>10 microns). Some implementations of the current subject matter use high intensity ultrasound below an amplitude that causes cavitation. Breakage of cell walls and cellular membranes of microorganisms occurs due to the high pressures caused at the nodes of the acoustic standing wave. As an example of the potential of this approach, a suspension of concentrated microalgae of mixed sizes (mixed ages, 0.1 mm to 1.0 mm) of the nematode *Caenorhabditis elegans* were placed in a vertical glass tube with a PZT-4 2.3 MHz transducer mounted on the bottom with a glass plate on the top as the acoustic reflector. By simply subjecting the organisms to acoustophoresis without cavitation the smaller worms were crushed open and the larger organisms suffered catastrophic neuromuscular problems. This occurred when the pressure amplitude was about 0.5 MPa at the acoustic nodes.

In further implementations, a cavitation technique can be incorporated as a pre-treatment step. A system such as that shown in FIG. 1 can be operated in cavitation mode to enhance the killing of microorganisms in the size scale from 1 micron to 100 microns. During the cavitation process, the cell wall and cellular membranes can be broken and the proteins released from the cells. In one illustrative example, an acoustic field resulting in cavitation was applied for about five minutes. Within a few minutes most of the organism debris—the cell wall and cellular debris falls to the bottom of the acoustic chamber.

Example 3

Separating Iron Oxide Particles from Water Using an Acoustic Standing Wave

The current subject matter can also concentrate and/or remove micron-scale metal oxide particles. As a demonstration of this capability, 10 micron iron oxide particles were suspended in water and passed through the apparatus shown in FIG. 3. In this demonstration, the flow chamber is horizontal with the transducer on top facing downward. The acoustic standing wave is in the vertical direction. The transducer is a PZT-4 2 MHZ transducer. A peristaltic pump is used to generate fluid flow rates that are most typically about 50 ml/min.

Figure 6:
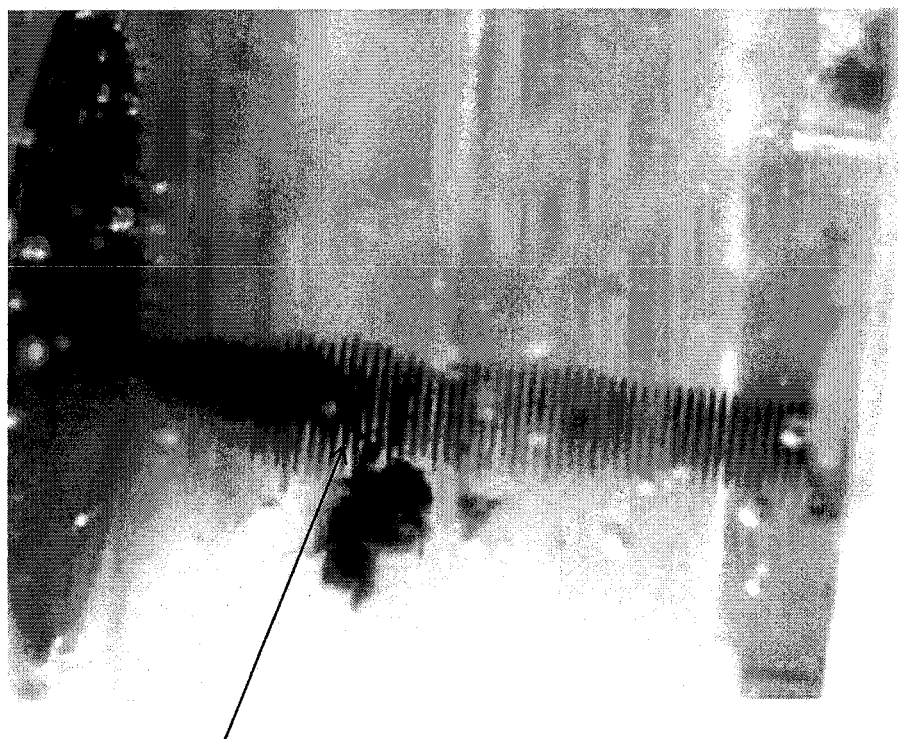
FIG. 6 shows a 10× magnification photograph showing collection of iron oxide particles from flowing water [601] in an acoustic chamber.

The acoustic transducer is connected to an amplifier which receives its signal from a function generator and operates at about $15 V_{rms}$. Once the fluid flow and the acoustic transducer are turned on, trapping and concentration of iron oxide begins instantaneously or nearly instantaneously. The oxide particles are trapped in the acoustic field against the fluid drag force by means of the action of the acoustic radiation force. The photomicrograph of FIG. 6 illustrates the results of such a test.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claim.

The invention claimed is:

1. A method of separating particulate from a fluid comprising:
    flowing the fluid past two or more positions; and
    forming three dimensional acoustic standing waves at the two or more positions, wherein each acoustic standing wave is maintained at a different ultrasonic frequency, wherein each ultrasonic frequency is optimized for a specific range of particle sizes, and wherein particulate of the optimized size is trapped in its corresponding acoustic standing wave against the flow of the fluid, thereby concentrating the particulate in its corresponding acoustic standing wave;
    wherein the two or more three dimensional acoustic standing waves are pulsed waveforms resulting in high intensity acoustic pressure.

2. The method of claim 1, wherein at least one of the pulsed waveforms results in the high intensity acoustic pressure having sufficient amplitude to rupture the cell wall and cellular membranes of microorganisms.

3. The method of claim 1, wherein at least one of the pulsed waveforms results in the high intensity acoustic pressure having sufficient amplitude to cause cavitation.

4. The method of claim 1, wherein the particulate is selected from the group consisting of microalgae, yeast, fungi, bacteria, spores, gases or oils, metal oxides, metal particles, clays, dirt, plastics, and any particulate with a non-zero contrast factor.

5. The method of claim 1, further comprising sweeping the frequency of the three dimensional acoustic standing wave at one of the two or more positions, thereby directing the concentrated particulate into a collection pocket.

6. The method of claim 5, wherein the collection pocket is planar, conical, curved, or spherical in shape; and wherein the collection pocket further comprises a first door sealing the collection pocket away from the fluid.

7. The method of claim 6, wherein the collection pocket connects to a conduit, and wherein the conduit further comprises a second door which prevents entry of the fluid into the conduit when the first door is open.

8. The method of claim 1, further comprising electrochemically generating ozone.

9. The method of claim 1, wherein the three dimensional acoustic standing waves are generated by ultrasonic transducers driven by a voltage amplitude of between 1 and 100 volts (DC).

10. The method of claim 1, wherein each position includes an ultrasonic transducer and a reflector for forming the three dimensional acoustic standing wave at the position.

11. The method of claim 10, wherein the ultrasonic transducer at each position is made of a piezo-electric material.

12. The method of claim 1, wherein the three dimensional acoustic standing waves at the two or more positions are perpendicular to the direction of mean flow.

13. The method of claim 1, wherein each ultrasonic frequency is from 1 kHz to 100 MHz.

14. The method of claim 1, wherein the two or more acoustic standing waves are perpendicular to a direction of mean flow in a flow chamber.

15. The method of claim 1, wherein the three dimensional acoustic standing waves have a horizontal orientation or a vertical orientation.

16. The method of claim 1, wherein the frequency of excitation of the three dimensional acoustic standing waves is constant.

17. A method of separating particulate from a fluid comprising:
    flowing the fluid past two or more positions; and
    forming three dimensional acoustic standing waves at the two or more positions, wherein each acoustic standing wave is maintained at a different ultrasonic frequency, wherein each ultrasonic frequency is optimized for a specific range of particle sizes, and wherein particulate of the optimized size is trapped in its corresponding acoustic standing wave against the flow of the fluid, thereby concentrating the particulate in its corresponding acoustic standing wave;
    wherein the three dimensional acoustic standing waves are generated by ultrasonic transducers driven by a voltage amplitude of between 1 and 100 volts (DC).

18. The method of claim 17, wherein the particulate is selected from the group consisting of microalgae, yeast, fungi, bacteria, spores, gases or oils, metal oxides, metal particles, clays, dirt, plastics, and any particulate with a non-zero contrast factor.

19. The method of claim 17, further comprising sweeping the frequency of the three dimensional acoustic standing wave at one of the two or more positions, thereby directing the concentrated particulate into a collection pocket.

20. The method of claim 19, wherein the collection pocket is planar, conical, curved, or spherical in shape; and wherein the collection pocket further comprises a first door sealing the collection pocket away from the fluid.

21. The method of claim 20, wherein the collection pocket connects to a conduit, and wherein the conduit further comprises a second door which prevents entry of the fluid into the conduit when the first door is open.

22. The method of claim 17, wherein the two or more three dimensional acoustic standing waves are pulsed waveforms resulting in high intensity acoustic pressure.

23. The method of claim 22, wherein at least one of the pulsed waveforms results in the high intensity acoustic pressure having sufficient amplitude to rupture the cell wall and cellular membranes of microorganisms.

24. The method of claim 22, wherein at least one of the pulsed waveforms results in the high intensity acoustic pressure having sufficient amplitude to cause cavitation.

25. The method of claim 17, further comprising electrochemically generating ozone.

26. The method of claim 17, wherein each position includes an ultrasonic transducer and a reflector for forming the three dimensional acoustic standing wave at the position.

27. The method of claim 26, wherein the ultrasonic transducer at each position is made of a piezo-electric material.

28. The method of claim 17, wherein the three dimensional acoustic standing waves at the two or more positions are perpendicular to the direction of mean flow.

29. The method of claim 17, wherein each ultrasonic frequency is from 1 kHz to 100 MHz.

30. The method of claim 17, wherein the two or more acoustic standing waves are perpendicular to a direction of mean flow in a flow chamber.

31. The method of claim 17, wherein the three dimensional acoustic standing waves have a horizontal orientation or a vertical orientation.

32. The method of claim 17, wherein the frequency of excitation of the three dimensional acoustic standing waves is constant.

33. A method of separating particulate from a fluid comprising:
flowing the fluid past two or more positions;
forming three dimensional acoustic standing waves at the two or more positions, wherein each acoustic standing wave is maintained at a different ultrasonic frequency, wherein each ultrasonic frequency is optimized for a specific range of particle sizes, and wherein particulate of the optimized size is trapped in its corresponding acoustic standing wave against the flow of the fluid, thereby concentrating the particulate in its corresponding acoustic standing wave; and
sweeping the frequency of the three dimensional acoustic standing wave at one of the two or more positions, thereby directing the concentrated particulate into a collection pocket.

34. The method of claim 33, wherein the particulate is selected from the group consisting of microalgae, yeast, fungi, bacteria, spores, gases or oils, metal oxides, metal particles, clays, dirt, plastics, and any particulate with a non-zero contrast factor.

35. The method of claim 33, wherein the two or more three dimensional acoustic standing waves are pulsed waveforms resulting in high intensity acoustic pressure.

36. The method of claim 35, wherein at least one of the pulsed waveforms results in the high intensity acoustic pressure having sufficient amplitude to rupture the cell wall and cellular membranes of microorganisms.

37. The method of claim 35, wherein at least one of the pulsed waveforms results in the high intensity acoustic pressure having sufficient amplitude to cause cavitation.

38. The method of claim 33, further comprising electrochemically generating ozone.

39. The method of claim 33, wherein the three dimensional acoustic standing waves are generated by ultrasonic transducers driven by a voltage amplitude of between 1 and 100 volts (DC).

40. The method of claim 33, wherein each position includes an ultrasonic transducer and a reflector for forming the three dimensional acoustic standing wave at the position.

41. The method of claim 40, wherein the collection pocket is positioned on the transducer or on the wall of the flow chamber opposite the transducer; wherein the collection pocket is planar, conical, curved, or spherical in shape; and wherein the collection pocket further comprises a first door sealing the collection pocket away from the fluid.

42. The method of claim 41, wherein the collection pocket connects to a conduit, and wherein the conduit further comprises a second door which prevents entry of the fluid into the conduit when the first door is open.

43. The method of claim 40, wherein the two or more ultrasonic transducers are made of a piezo-electric material.

44. The method of claim 33, wherein the three dimensional acoustic standing waves at the two or more positions are perpendicular to the direction of mean flow.

45. The method of claim 33, wherein each ultrasonic frequency is from 1 kHz to 100 MHz.

46. The method of claim 33, wherein the two or more acoustic standing waves are perpendicular to a direction of mean flow in a flow chamber.

47. The method of claim 33, wherein the three dimensional acoustic standing waves have a horizontal orientation or a vertical orientation.

48. The method of claim 33, wherein the frequency of excitation of the three dimensional acoustic standing waves is constant.

* * * * *